United States Patent [19]

Allen et al.

[11] Patent Number: 4,959,378

[45] Date of Patent: Sep. 25, 1990

[54] AMINOPYRIDINYLAMINOPHENOL COMPOUNDS USEFUL AS TOPICAL ANTIINFLAMMATORY AGENTS FOR THE TREATMENT OF SKIN DISORDERS

[75] Inventors: Richard C. Allen, Flemington; Joseph T. Klein; Richard C. Effland, both of Bridgewater, all of N.J.

[73] Assignee: Hoechst-Roussel Pharmaceuticals Inc., Somerville, N.J.

[21] Appl. No.: 425,713

[22] Filed: Oct. 24, 1989

[51] Int. Cl.$^5$ .................... A61K 31/44; C07D 213/26
[52] U.S. Cl. ................................ 514/352; 546/307; 546/308
[58] Field of Search ................ 514/349, 352, 353; 546/307, 308

[56] References Cited

U.S. PATENT DOCUMENTS

| | | | |
|---|---|---|---|
| 3,118,884 | 1/1964 | Clarke | 544/34 |
| 3,495,969 | 2/1970 | Driscoll | |
| 3,576,616 | 4/1971 | Nowotny | 71/76 |
| 3,721,676 | 3/1973 | Witzel | 546/297 |
| 3,835,143 | 9/1974 | Witzel et al. | 546/297 |

FOREIGN PATENT DOCUMENTS

| | | | |
|---|---|---|---|
| 0069885 | 9/1987 | Australia | 546/297 |
| 0110405 | 6/1984 | European Pat. Off. | 546/297 |
| 2073736 | 10/1981 | United Kingdom | 546/297 |

OTHER PUBLICATIONS

Brewster et al., J. Heterocyclic Chem., vol. 15, 1975, p. 1497.
Butler et al., J. Med. Chem., vol. 24, 1981, pp. 346–350.
Ito et al., Pharm. Bull., vol. 26, No. 5, 1978, pp. 1375–1383.
Lowry et al., An Introduction to Organic Chemistry, 1953, p. 266.

*Primary Examiner*—Mary C. Lee
*Assistant Examiner*—Zinna Northington-Davis
*Attorney, Agent, or Firm*—Tatsuya Ikeda

[57] ABSTRACT

There are described compounds of the formula

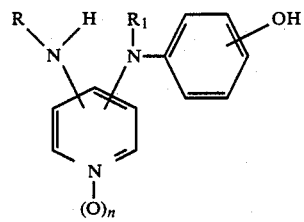

where
R is hydrogen, loweralkyl, arylloweralkyl or loweralkylcarbonyl;
$R_1$ is hydrogen, loweralkyl or loweralkylcarbonyl; and
n is 0 or 1;

which compounds are useful as topical antiinflammatory agents for the treatment of various dermatoses.

20 Claims, No Drawings

AMINOPYRIDINYLAMINOPHENOL COMPOUNDS USEFUL AS TOPICAL ANTIINFLAMMATORY AGENTS FOR THE TREATMENT OF SKIN DISORDERS

The present invention relates to compounds of Formula I,

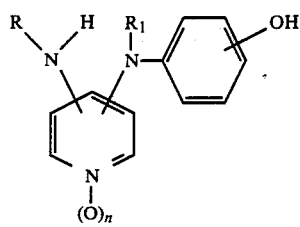
(I)

where
- R is hydrogen, loweralkyl, arylloweralkyl or loweralkylcarbonyl;
- $R_1$ is hydrogen, loweralkyl or loweralkylcarbonyl; and
- n is 0 or 1.

which compounds are useful as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of Formula II where n and $R_1$ are as defined above, which are useful for the same dermatological applications as mentioned above and also as direct precursors of the compounds of Formula I.

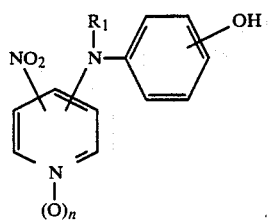
(II)

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-cutyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

Throughout the specification and the appended claims, a given chemical formula or name shall encompass all stereo, optical, geometrical and tautomeric isomers where such isomers exist.

The compounds of this invention are prepared by utilizing one or more of the synthetic steps described below.

Throughout the description of the synthetic steps, the notations n, R and $R_1$ shall have the respective meanings given above unless otherwise stated or indicated, and other notations shall have the respective meanings defined in their first appearances unless otherwise stated or indicated.

STEP A:

A compound of Formula III where Hal is F or Cl, preferably F, is allowed to react with a compound of Formula IV to afford a compound of Formula V.

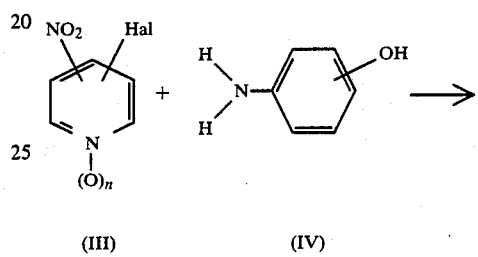

(III)            (IV)

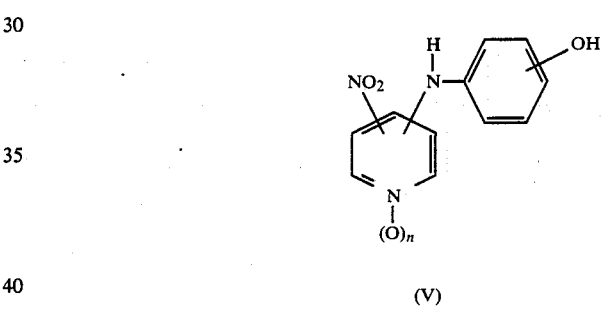

(V)

This reaction is typically conducted in a suitable solvent such as ethanol, dimethylformamide, dimethylsulfoxide or N-methylpyrrolidone at a temperature of about 0° to 150° C.

3-Fluoro-4-nitropyridine-1-oxide, which belongs to the group of compounds of Formula III, is disclosed in Talik and Talik, Roczniki Chemii, Volume 38, 777 (1964). 4-Chloro-3-nitropyridine, which also belongs to the group of compounds of Formula III, is disclosed in Talik and Talik, Roczniki Chemii, Volume 43, 923 (1969).

STEP B:

Compound V is allowed to react with a compound of the formula $R_1$—Hal, where $R_1$ is loweralkyl or loweralkylcarbonyl and Hal is bromine or chlorine in a routine manner known to the art to afford a compound of Formula II.

(V)+$R_1$—Hal→(II)

STEP C:

A compound of Formula IIa is selectively hydrogenated to afford a compound of Formula VI.

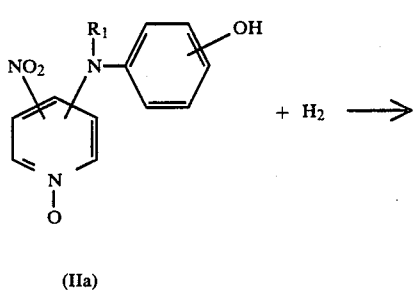

(IIa)

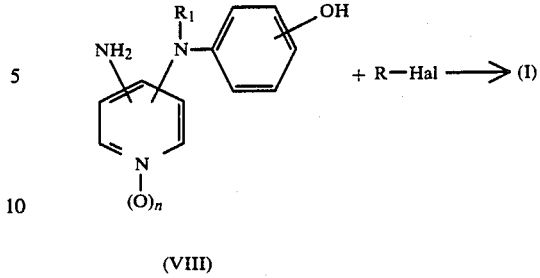

(VIII)

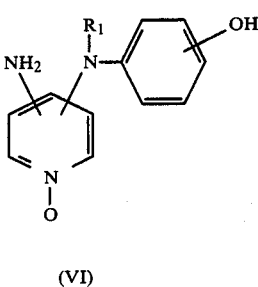

(VI)

This selective hydrogenation is typically conducted with the aid of a suitable catalyst such as Pd/C or PtO₂ and a suitable medium such as ethanol at a temperature of about 20° to 100° C.

STEP D:

Compound IIa is catalytically hydrogenated in a manner similar to the one described in STEP C above, except that a longer reaction period or higher reaction temperature is preferably employed, to afford a compound of Formula VII.

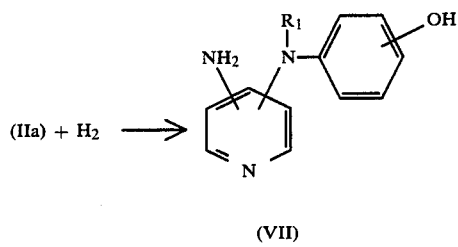

(VII)

Instead of using compound IIa in the above reaction, one can also use compound VI and conduct the hydrogenation in substantially the same manner as described above to obtain compound VII.

STEP E:

A compound of Formula VIII obtained from STEP C or D is allowed to react with a compound of the formula, R—Hal, where R is loweralkyl, arylloweralkyl or loweralkylcarbonyl and Hal is bromine or chlorine, in a routine manner known to the art to afford a compound of Formula I.

Compounds of Formula I and Formula II according to this invention are useful as topical agents for the treatment of various skin disorders such as those mentioned earlier. The dermatological activities of the compounds of this invention were ascertained with reference to the following methods.

DERMATOLOGICAL TEST METHODS

Phospholipase A₂-induced Paw Edema (PIPE)

The ability of compounds to prevent naja naja (snake venom) phospholipase A₂-induced paw edema in male Wistar rates (100–125 g) was measured. PLA₂(3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone ED$_{50}$=0.46M). See Giessler, A. J. et al., *Agents and Actions*, Vol. 10, Trends in Inflammation Research (1981), p. 195.

In Vitro Phospholipase A₂ Assay (PLA₂)

The ability of a compound to modulate PLA₂ activity (cleavage of $^{14}$C-dipalmitoyl phosphotidylcholine at the 2-position to $^{14}$C-palmitic acid) was quantitated in this assay. The reaction mixture contained Tris buffer (25 mM), pH 8.0, calcium chloride (2.0 mM), bovine serum albumin (0.5 mg), dipalmitoyl phosphotidylcholine (8×10$^{-5}$M), ($^{14}$C-palmitoyl)dipalmitoyl phosphotidylcholine (6×10$^3$ cpm), porcine pancreatic PLA₂ (3.2 units) and the test compound. The reaction was run at 37° C. in a shaking incubator. The reaction was quenched and an internal standard was added in order to determine sample recovery. The samples were loaded onto C$_{18}$ columns, eluted with ethanol, and the radioactivity was then measured. (Standard: quinacrine IC$_{50}$=3.5×10$^{-4}$M). See Feyen, J. H. M., et al., *Journal of Chromatography* 259 (1983), pp. 338–340.

Dermatological activities for some of the compounds of this invention are presented in Table 1.

TABLE 1

| Compound | PIPE* (0.1 M) | PLA₂* (0.01 M) |
| --- | --- | --- |
| 3-[(4-Amino-3-pyridinyl)amino]phenol | −52% | −35% |
| 4-[(4-Amino-3-pyridinyl)amino]phenol maleate | −62% | −35% |

*difference in edema vs. control

Examples of the compounds of this invention include:
3-[(4-Nitro-3-pyridinyl)amino]phenol, N-oxide;
4-[(4-Nitro-3-pyridinyl)amino]phenol, N-oxide;

3-[(4-Amino-3-pyridinyl)amino]phenol;
4-[(4-Amino-3-pyridinyl)amino]phenol;
3-[(3-Nitro-4-pyridinyl)amino]phenol;
4-[(4-Nitro-3-pyridinyl)propylamino]phenol, N-oxide;
3-[(3-Amino-4-pyridinyl)amino]phenol;
4-[(4-Amino-3-pyridinyl)propylamino]phenol;
4-[(3-Amino-4-pyridinyl)benzylamino]phenol; and
N-[3-(4-Hydroxyphenyl)amino-4-pyridinyl]acetamide;

The following examples are presented in order to illustrate this invention. All temperatures are give in degrees Celcius.

EXAMPLE 1

3-[(4-Nitro-3-pyridinyl)amino]phenol, N-oxide

A solution of 3-fluoro-4-nitropyridine-N-oxide[1] (7 g) and 3-aminophenol (5 g) in 250 ml ethanol was stirred at reflux for two hours and thereafter cooled, diluted with ether and filtered to yield 11 g solid, d 240°. Three grams were triturated in hot methanol for one hour and thereafter cooled, collected and dried to yield 2.9 g solid, d 257°–258°.

[1]Talik and Talik; Roczniki Chemii, 38, 777 (1964)

| Analysis: | | | |
|---|---|---|---|
| Calculated for $C_{11}H_9N_3O_4$: | 53.45% C | 3.67% H | 17.00% N |
| Found: | 53.28% C | 3.60% H | 16.94% N |

EXAMPLE 2

4-[(4-Nitro-3-pyridinyl)amino]phenol, N-oxide

A solution of 3-fluoro-4-nitropyridine-N-oxide (7 g) and 4-aminophenol (5 g) in 250 ml ethanol was stirred at reflux for two hours and thereafter cooled, diluted with ether and filtered to yield 10.7 g solid. This solid was triturated in hot methanol for one hour and thereafter cooled, collected and dried to yield 10.5 g solid, d 265°. A 2.5 g portion was triturated with hot methanol for one hour and thereafter cooled, collected and dried to yield 2.3 g solid, d 275°.

| Analysis: | | | |
|---|---|---|---|
| Calculated for $C_{11}H_9N_3O_4$: | 53.45% C | 3.67% H | 17.00% N |
| Found: | 52.97% C | 3.67% H | 16.90% N |

EXAMPLE 3

3-[(4-Amino-3-pyridinyl)amino]phenol

A suspension of 3-[(4-nitro-3-pyridinyl)amino]phenol, N-oxide (6.2 g) in 250 ml ethanol containing 0.6 g platinum oxide was hydrogenated at 60 psi (pounds per square inch) for five hours and thereafter filtered through Celite and concentrated to 5 g oil. This was purified by flash chromatography (silica, 25% methanol in dichloromethane) to give 4.5 g solid. This was recrystallized from acetonitrile to give 3.9 g crystals, mp 174°–176°. This solid was recrystallized from acetonitrile to yield 3.2 g crystals, mp 175°–177°.

| Analysis: | | | |
|---|---|---|---|
| Calculated for $C_{11}H_{11}N_3O$: | 65.66% C | 5.51% H | 20.89% N |
| Found: | 65.56% C | 5.51% H | 20.95% N |

EXAMPLE 4

4-[(4-Amino-3-pyridinyl)amino]phenol maleate

A suspension of 4-[(4-nitro-3-pyridinyl)amino]phenol, N-oxide (9 g) in 250 ml ethanol containing 0.6 g platinum oxide was hydrogenated at 60 psi for 16 h and thereafter filtered through Celite and concentrated to 6 g solid. This was purified by flash chromatography (silica, 25% methanol in dichloromethane) to yield 4 g solid. This was again purified by flash chromatography (silica, 25% methanol in dichloromethane) to yield 2.9 g solid which was immediately converted to the maleate salt in methanol/ether to yield 3.2 g solid, d 173°. This solid was recrystallized from methanol/ether to yield 2.7 g crystals, d 179°–180°.

| Analysis: | | | |
|---|---|---|---|
| Calculated for $C_{15}H_{15}N_3O_5$: | 56.78% C | 4.77% H | 13.25% N |
| Found: | 56.78% C | 4.73% H | 13.29% N |

We claim:

1. A compound having the formula,

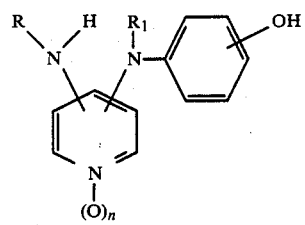

where
R is hydrogen, loweralkyl, arylloweralkyl or loweralkylcarbonyl;
$R_1$ is hydrogen, loweralkyl or loweralkylcarbonyl; and
n is 0 or 1;
the term aryl signifying a phenyl group optionally mono-substituted with a loweralkyl, loweralkoxy, halogen or trifluoromethyl group; or a pharmaceutically acceptable acid addition salt thereof.

2. The compound as defined in claim 1, wherein $R_1$ is hydrogen.

3. The compound as defined in claim 1, where R is hydrogen.

4. The compound as defined in claim 1, where $R_1$ is hydrogen and R is hydrogen.

5. The compound as defined in claim 1, which is 3-[(4-amino-3-pyridinyl)amino]phenol.

6. The compound as defined in claim 1, which is 4-[(4-amino-3-pyridinyl)amino]phenol.

7. The compound as defined in claim 1, which is 3-[(3-amino-4-pyridinyl)amino]phenol.

8. The compound as defined in claim 1, which is 4-[(4-amino-3-pyridinyl)propylamino]phenol.

9. The compound as defined in claim 1, which is 4-[(3-amino-4-pyridinyl)benzylamino]phenol.

10. The compound as defined in claim 1, which is N-[3-(4-hydroxyphenyl)amino-4-pyridinyl]acetamide.

11. A dermatological composition which comprises a compound as defined in claim 1 in an amount effective for treating a skin disorder, and a suitable carrier therefor.

12. A method of treating a patient in need of relief from a skin disorder, which comprises administering to such a patient an effective amount of a compound as defined in claim 1.

13. A compound having the formula,

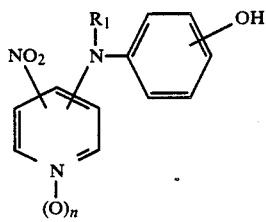

where
n is 0 or 1; and
$R_1$ is hydrogen, loweralkyl or loweralkycarbonyl;
or a pharmaceutically acceptable acid addition salt thereof.

14. The compound as defined in claim 13, where $R_1$ is hydrogen.

15. The compound as defined in claim 13, which is 3-[(4-nitro-3-pyridinyl)amino]phenol.

16. The compound as defined in claim 13, which is 4-[(4-nitro-3-pyridinyl)amino]phenol.

17. The compound as defined in claim 13, which is 3-[(3-nitro-4-pyridinyl)amino]phenol.

18. The compound as defined in claim 13, which is 4-[(4-nitro-3-pyridinyl)propylamino]phenol, N-oxide.

19. A dermatological composition which comprises a compound as defined in claim 13 in an amount effective for treating a skin disorder, and a suitable carrier therefor.

20. A method of treating a patient in need of relief from a skin disorder, which comprises administering to such a patient an effective amount of a compound as defined in claim 13.

* * * * *

REEXAMINATION CERTIFICATE (2074th)
United States Patent [19]
Allen et al.

[11] B1 4,959,378
[45] Certificate Issued Aug. 10, 1993

[54] AMINOPYRIDINYLAMINOPHENOL COMPOUNDS USEFUL AS TOPICAL ANTIINFLAMMATORY AGENTS FOR THE TREATMENT OF SKIN DISORDERS

[75] Inventors: Richard C. Allen, Flemington; Joseph T. Klein; Richard C. Effland, both of Bridgewater, all of N.J.

[73] Assignee: Hoechst-Roussel Pharmaceuticals Inc., Sommerville, N.J.

Reexamination Request:
No. 90/002,445, Sep. 23, 1991

Reexamination Certificate for:
Patent No.: 4,959,378
Issued: Oct. 24, 1989
Appl. No.: 425,713
Filed: Sep. 25, 1990

[51] Int. Cl.$^5$ .................... A61K 31/44; C07D 213/74
[52] U.S. Cl. ................................. 514/352; 546/307; 546/308
[58] Field of Search .................. 546/307, 308; 514/352

[56] References Cited

U.S. PATENT DOCUMENTS

| | | | |
|---|---|---|---|
| 3,118,884 | 1/1964 | Clark | 260/243 |
| 3,375,257 | 3/1968 | Thiele et al. | 260/295 |
| 3,474,107 | 10/1969 | Thiele | 260/295.5 |
| 3,495,969 | 2/1970 | Driscoll | 71/94 |
| 3,567,765 | 3/1971 | Thiele | 260/490 |
| 3,576,616 | 4/1971 | Nowotny | 71/94 |
| 3,719,762 | 3/1973 | Thiele | 424/324 |
| 3,721,676 | 3/1973 | Witzel | 260/296 R |
| 3,835,143 | 9/1974 | Witzel et al. | 260/247.1 |

FOREIGN PATENT DOCUMENTS

| | | |
|---|---|---|
| 0069885 | 9/1987 | Australia . |
| 668738 | 12/1965 | Belgium . |
| 0110405 | 6/1984 | European Pat. Off. . |
| 1795499 | 2/1972 | Fed. Rep. of Germany . |
| 1795544 | 2/1973 | Fed. Rep. of Germany . |
| 3334030 | 4/1985 | Fed. Rep. of Germany . |
| 1401469 | 4/1965 | France . |
| 750925 | 6/1956 | United Kingdom . |
| 2073736 | 10/1981 | United Kingdom . |

OTHER PUBLICATIONS

Delarge et al., Pharm. Acta Helv, 50(6), pp. 188–191 (1975).
Ito et al., Chem. Pharm. Bull., 26(5), pp. 1375–1383 (1978).
Takahishi et al., Chem. Pharm. Bull., 6, pp. 46–49 (1958).
Kaczmarek et al., Polish J. Pharmacol. Pharm., 33(1), pp. 121–127 (1981); Chem. Abstracts vol. 95, 97631d (1981).
Chem. Abstracts 2918b, vol. 48 (1954).
Chem. Abstracts 4837b, vol. 61 (1963).

*Primary Examiner*—Bernard Dentz

[57] ABSTRACT

There are described compounds of the formula

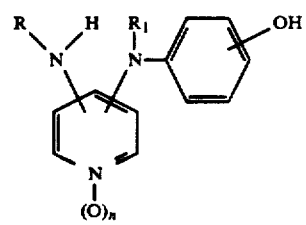

where
R is hydrogen, loweralkyl, arylloweralkyl or loweralkylcarbonyl;
R$_1$ is hydrogen, loweralkyl or loweralkylcarbonyl; and
n is 0 or 1;

which compounds are useful as topical antiinflammatory agents for the treatment of various dermatoses.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9, 11–13, 17, 19 and 20 are cancelled.

Claims 2–8, 10, 14–16 and 18 are determined to be patentable as amended.

New claims 21–26 are added and determined to be patentable.

2. The compound as defined in claim [1] *22*, wherein $R_1$ is hydrogen.

3. The compound as defined in claim [1] *22*, where R is hydrogen.

4. The compound as defined in claim [1] *22*, where $R_1$ is hydrogen and R is hydrogen.

5. The compound as defined in claim [1] *22*, which is 3-[(4-amino-3-pyridinyl)amino]phenol.

6. The compound as defined in claim [1] *22*, which is 4-[(4-amino-3-pyridinyl)amino]phenol.

7. The compound as defined in claim [1] *22*, which is 3-[(3-amino-4-pyridinyl)amino]phenol.

8. The compound as defined in claim [1] *22*, which is 4-[(4-amino-3-pyridinyl)propylamino]phenol.

10. The compound as defined in claim [1] *22*, which is N-[3-(4-hydroxyphenyl)amino-4-pyridinyl]acetamide.

14. The compound as defined in claim [13] *21*, where $R_1$ is hydrogen.

15. The compound as defined in claim [13] *21*, which is 3-[(4-nitro-3-pyridinyl)amino]phenol.

16. The compound as defined in claim [13] *21*, which is 4-[(4-nitro-3-pyridinyl)amino]phenol.

18. The compound as defined in claim [13] *21*, which is 4-[(4-nitro-3-pyridinyl)propylamino]phenol, N-oxide.

*21. A compound having the formula*

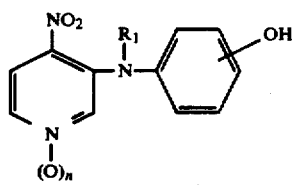

*where*
*n is 0 or 1; and*
*$R_1$ is hydrogen, loweralkyl or loweralkylcarbonyl; or a pharmaceutically acceptable acid addition salt thereof.*

*22. A compound of the formula*

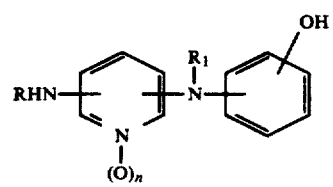

*where*
*R is hydrogen, loweralkyl, arylloweralkyl or loweralkylcarbonyl;*
*$R_1$ is hydrogen, loweralkyl or loweralkylcarbonyl; and*
*n is 0 or 1;*
*the term aryl signifying a phenyl group optionally mono-substituted with a loweralkyl, loweralkoxy, halogen or trifluoromethyl group; or a pharmaceutically acceptable acid addition salt thereof,*
*where the aminophenyl group and the —NHR group are each attached at the 3- or 4-position of the pyridine ring.*

*23. A dermatological composition which comprises the compound of claim 22 in an amount effective for treating a skin disorder, and a suitable carrier thereof.*

*24. A method of treating a patient in need of relief from a skin disorder, which comprises administering to such a patient an effective amount of a compound of claim 22.*

*25. A dermatological composition which comprises a compound of claim 21 in an amount effective for treating a skin disorder, and a suitable carrier therefor.*

*26. A method of treating a patient in need of relief from a skin disorder, which comprises administering to such a patient an effective amount of the compound of claim 21.*

* * * * *